United States Patent
Muller

(10) Patent No.: US 8,603,100 B2
(45) Date of Patent: Dec. 10, 2013

(54) SURGICAL TOOL AND METHOD

(76) Inventor: Erich Johann Muller, Kleinwallstadt (DE)

( * ) Notice: Subject to any disclaimer, the term of this patent is extended or adjusted under 35 U.S.C. 154(b) by 1139 days.

(21) Appl. No.: 12/097,719

(22) PCT Filed: Dec. 15, 2005

(86) PCT No.: PCT/DE2005/002271
§ 371 (c)(1),
(2), (4) Date: Jun. 16, 2008

(87) PCT Pub. No.: WO2007/068219
PCT Pub. Date: Jun. 21, 2007

(65) Prior Publication Data
US 2008/0262503 A1  Oct. 23, 2008

(51) Int. Cl.
*A61B 17/92* (2006.01)

(52) U.S. Cl.
USPC .................. 606/100; 606/99; 81/126

(58) Field of Classification Search
USPC .............. 606/99, 100, 104; 81/126, 128, 148, 81/358
See application file for complete search history.

(56) References Cited

U.S. PATENT DOCUMENTS

| | | | | |
|---|---|---|---|---|
| 1,810,938 A * | 6/1931 | Baash et al. | | 81/98 |
| 1,921,281 A * | 8/1933 | Carlson | | 81/126 |
| 2,094,190 A * | 9/1937 | Robinson | | 81/126 |
| 2,528,941 A * | 11/1950 | Bassett et al. | | 606/99 |
| 3,564,956 A * | 2/1971 | Landen | | 81/126 |
| 3,818,514 A * | 6/1974 | Clark | | 623/22.12 |
| 3,857,389 A * | 12/1974 | Amstutz | | 606/86 R |
| 4,222,382 A * | 9/1980 | Antonsson et al. | | 606/100 |
| 4,457,306 A * | 7/1984 | Borzone | | 606/1 |
| 4,642,121 A * | 2/1987 | Keller | | 623/22.12 |
| 4,686,971 A * | 8/1987 | Harris et al. | | 606/99 |
| 5,196,018 A * | 3/1993 | Willert et al. | | 606/99 |
| 5,534,006 A * | 7/1996 | Szabo et al. | | 606/100 |
| 6,626,913 B1 * | 9/2003 | McKinnon et al. | | 606/99 |
| 6,679,888 B2 * | 1/2004 | Green et al. | | 606/86 R |
| 7,708,743 B2 * | 5/2010 | Anderson et al. | | 606/99 |

* cited by examiner

*Primary Examiner* — Ralph Lewis
(74) *Attorney, Agent, or Firm* — Baker & Hostetler LLP

(57) ABSTRACT

Surgical tool for knocking out and/or inserting of prostheses (1), in particular joint prostheses, in particular hip and/or shoulder prostheses, with in particular continuously curved head (2) of the tool, which exhibits a passage (3) for the seating of a prosthesis neck (4) and a bolt mechanism, which blocks detachably the neck (4) of the prosthesis in the passage (3), whereby the bolt mechanism exhibits an blocking element (5) intervening in the passage (3), which interference position is adaptable to different diameters of the neck (4) of the prosthesis, whereby an adjusting force is to be applied on the blocking element (5) by means of a adjustment member (6), where the manipulation of the adjustment member (5) is to be arranged by an adjustment element (7) outside of the operation field with distance to the blocking element (5).

17 Claims, 9 Drawing Sheets

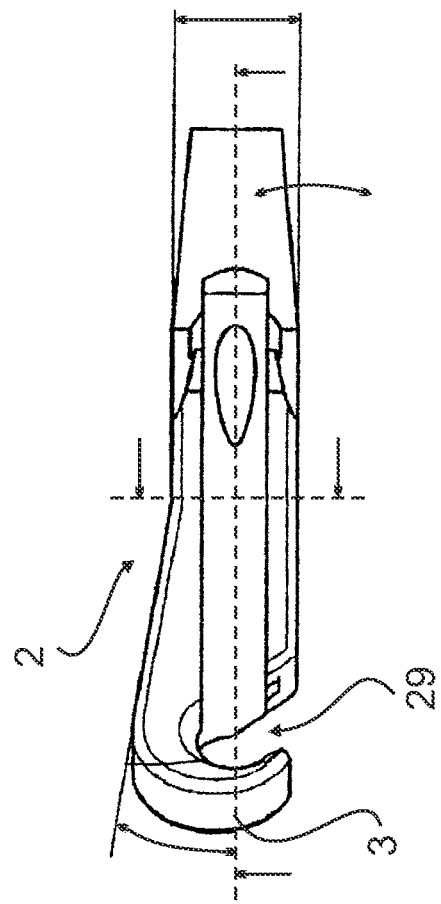
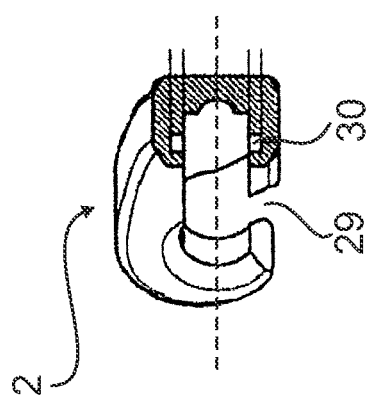

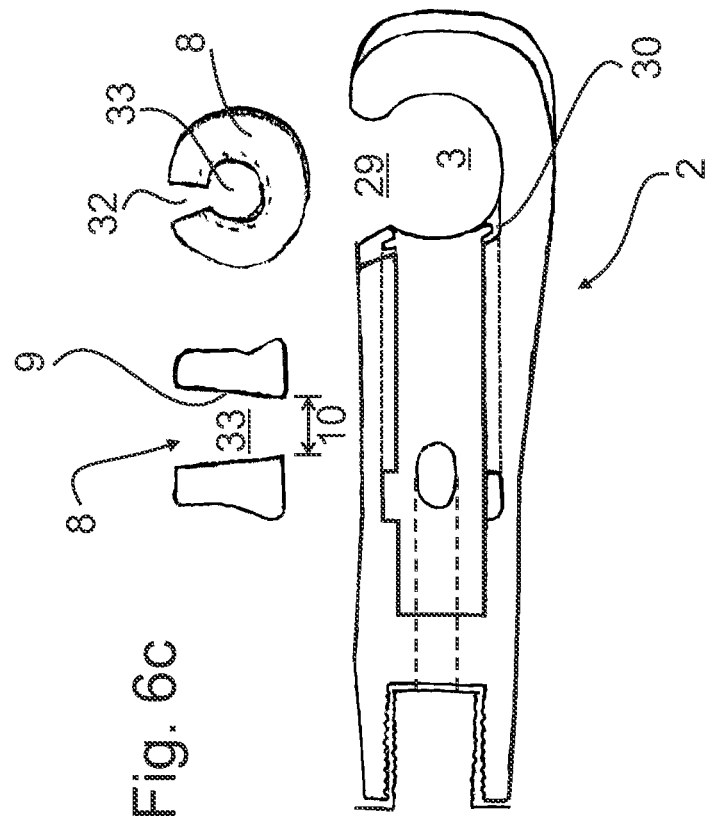

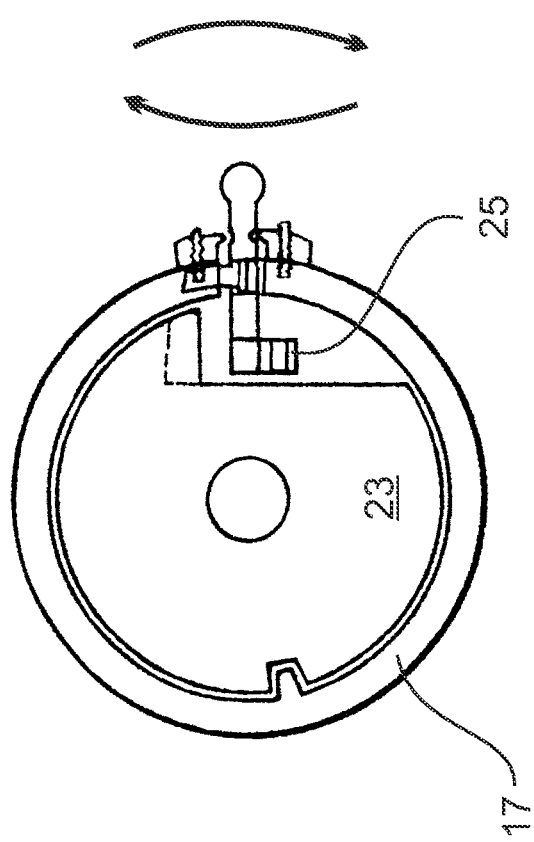

SURGICAL TOOL AND METHOD

FIELD OF THE INVENTION

The invention regards a surgical tool for knocking out and/or inserting of prostheses, in particular joint prostheses, in particular hip and/or shoulder prostheses.

BACKGROUND OF THE INVENTION

Well-known are surgical tools, which exhibit an adjustment device with complex construction made of many single parts and have an closely attached handling equipment for the fixation of the prosthesis.

SUMMARY OF THE INVENTION

It is an object of the present invention to provide a surgical tool, which facilitates an improved fixation of the tool at the prosthesis and a safe and targeted application of the force on the prosthesis.

The problem is solved by a Surgical tool for knocking out and/or inserting of prostheses, in particular joint prostheses, in particular hip and/or shoulder prostheses, with in particular continuously curved head of the tool, which exhibits a passage for the seating of a prosthesis neck and a bolt mechanism, which blocks detachably the neck of the prosthesis in the passage, whereby the bolt mechanism exhibits an blocking element intervening in the passage, which interference position is adaptable to different diameters of the neck of the prosthesis, whereby an adjusting force is to be applied on the blocking element by means of a adjustment member, where the manipulation of the adjustment member is to be arranged by an adjustment element outside of the operation field with distance to the blocking element.

The fixation of the prosthesis in the passage of the tool can be carried out by the distance of the adjustment device in an easy way out of the operation region. This allows an unhindered working for the surgeon and at the same time the actual condition in the operation region is not affected or changed. For example it is possible to implant a non cemented prosthesis with the tool, whereby the force impact takes place in the direction of the prosthesis. A non cemented and/or a cemented prosthesis can be removed by the invention in an easy and safe way.

The problem is solved as well by a surgical tool for knocking out and/or inserting of prostheses, in particular joint prostheses, in particular hip and/or shoulder prostheses with an in particular continuously curved head of the tool, which exhibits a passage for the seating of a prosthesis neck and a bolt mechanism, which detachable blocks the prosthesis neck in the passage, whereby the bolt mechanism exhibits a blocking element intervening in the passage, which interference position is adaptable to different diameters of the neck of the prosthesis, where an adjusting force is to be applied onto the blocking element by means of a controlling member, whereby the head of the tool exhibits an opening at a side of the passage for the lateral insertion of the prosthesis neck.

The lateral opening allows to work on prostheses, which are made monolithicly and which have no removable head, named monobloc prostheses. Additionally prostheses can be moved, for which it is difficult to release the head or for which a release of the head could effect a damage.

The problem is solved as well by a surgical tool for knocking out and/or inserting of prostheses, in particular joint prostheses, in particular hip and/or shoulder prostheses with an in particular continuously curved head of the tool, which exhibits a passage for the seating of a prosthesis neck and a bolt mechanism, which blocks the neck of the prosthesis detachably in the passage, whereby the bolt mechanism exhibits a blocking element intervening in the passage, which interference position is adaptable to different diameters of the neck of the prosthesis by the fact that a laterally opened, at least partial compressible insertion element with a substantially central seating for holding a prosthesis neck is inserted in the passage of the head of the tool.

With the help of the inserting element in the passage of the head of the tool easily damageable prostheses can be safely removed out of the inserting fixation or can be inserted. With the help of the inserting element the applied force is homogeneously distributed allover and this leads to a reduction of stress peaks especially in the region of the blocking member. The inner diameter of the inserting element can easily be adapted to the diameter of the neck of the prosthesis, whereby the outer diameter of the inserting element can remain substantially the same, adapted to the diameter of the passage of the tool. The inserting element can be inserted in passages with almost any form, whereby it has to be merely considered that the form of the seating has to be adapted to the form of the neck of the prosthesis.

It is advantageous if the laterally opened inserting element is inserted in the passage of the laterally opened head of the tool in that way, that the openings correspond to each other. The head of the tool can in this way be used for cheaper or elder monobloc prostheses, and for all other prostheses, which are easier to be inserted into the opening of the head of the tool and of the inserting element and at the same time are kept safely and without damages.

It is advantageous if the seating of the inserting element is made conically tapered and exhibits an inner diameter which is adapted to the respective diameter of a cone of the neck of a prosthesis. The neck of the prosthesis in particular shows a slightly concave tapered conus of the neck of the prosthesis, on which the head of the prosthesis can be mounted. By the conically tapered form of the seating of the inserting element the conus of the neck of the prosthesis is allover enclosed and the prosthesis can be moved at the conus of the neck of the prosthesis.

It is advantageous if the controlling member is a pull rod, which is to be actuated at an end, which is turned away from the head of the tool, by the adjustment element, where the adjustment element is to be inserted into a blocking position in the head of the tool for the heading and for the detachable blocking of the blocking member. By the use of the pull rod on the one hand a big distance to the head of the tool can be kept and at the same time the impact of the adjustment force is easier and safer.

An easy adaptable and variably adjustable adjustment device is provided, if the adjustment element by a lever with an eccentric head of the lever, which acts upon the end of the pull rod which is turned away from the toll, and defines a axially heading position of the blocking element, which is dependent on the pivoting angle.

He transport of the adjustment force is particularly reliable and safe if between head of the lever and the end of the pull rod, which is turned away from the head of the tool, a contact element, especially made of plastic, is arranged, which is elastic and strengthtransferring, too. The plastic is preferably chosen elastically, because a safe and enduring contact between the elements is established and at the same time the contact element will be so hard, that a sufficient transport of force between lever and pull rod is made possible.

An easy and reliable adjustment of the distance between head of the tool and adjustment element can be conducted, if the adjustment element is an adjustment housing, which exhibits a thread for adjustment, by which the distance between the head of the tool and the adjustment housing is adjustable. By the adjustment thread even bigger distances during the adjustment of the tool can be overcome, whereby in every intermediate status a safe hold of the elements of the tool is given by the engagement of the thread.

It is advantageous if the head of the lever is arranged in and/or at the adjustment housing. The adjustment of the thread effects a bigger adjustment of the distance of the adjustment elements and the pivoting of the lever effects simply the last, substantially shorter adjustment of the distance until the total contact of the adjustment element to the blocking member. Especially if the distance is very small already at the insertion of the neck of the prosthesis in the passage of the head of the tool, the sole adjustment of the adjustment contact by the layer can be sufficient.

It is advantageous, if a guiding housing, through which the pull rode is routed relocatable, exhibits at an end, which is turned to the head of the tool, a thread for the connection of the guiding housing and the head of the tool.

It is advantageous if the guiding housing at an end which is turned away from the head of the tool exhibits a thread as an connection to the adjustment housing, especially for the vernier adjustment in the sense of a additional adjustment element.

An easy an safe usability of the tool is given, if the guiding housing at an end which is turned away from the head of the tool, exhibits a thread as connection to a handhold, whereby the handhold is connected to the adjustment housing by a thread for the adjustment of the distance.

It is advantageous if the guiding housing serves as a handhold.

It is advantageous if the guiding housing on the outer diameter exhibits a relocatable impact grip, which is movable especially between head of the tool and adjustment housing.

A safely reproducible exertion of the power is possible if the impact power on the blocking member, which is engaged to the prosthesis in the head of the tool, is executed preferably by a power tool, which is capable of being adapted at an adapter at the adjustment housing. The power and the frequency of the impact can be easily adjusted by the power tool, for example adapted to the size and loading capacity of the prosthesis. Moreover the power tool can be used for other purposes, so that a multiple use exists and a saving of costs. The power tool can work for example pneumatically or electrically.

A very compact tool is provided, if the impact power is executed by expanding a tension spring, which is situated in the guiding housing, whereby the tension spring is applied by an impact-/holding element, which can be locked and unlocked, and after the unlocking the impact-/holding element beats against an end which is turned away from the head of the tool for the releasing of prosthesis or against an end which is turned towards the head of the tool for the insertion of the prosthesis.

An easily and safe applying of the tension is given, if the tension spring is to be clamped by movement of the adjacent impact-/holding element by a gear rod connected thereto and by a gear moving thereon, which is supported at the guiding housing.

A very easy and reliable tool is provided if the impact power is executed by impulsive hitting of an impact element, which is routed relocatably on the guiding housing, against an end, which is turned away from the head of the tool of the guiding housing and/or another element connected thereto for the releasing of the prosthesis or against an end, which is tuned towards the head of the tool, of the guiding housing for the inserting of the prosthesis. The direction of the applying of the force can be changed very easily without modification of the tool.

It is advantageous if the blocking member is guided by opposing grooves, which are formed in the head of the tool. By this the blocking member is kept safely and at the same time movable easily, so that an easy adaption to the neck of the prosthesis is possible.

It is advantageous for the adaption to smaller prosthesis if the blocking member is formed longer, so that the smaller necks of the prostheses are engaged in particular between 8 to 12 mm.

It is advantageous for the adaption to bigger prosthesis if the blocking member is formed shorter, so that broader necks of the prostheses are engaged in particular between 11 and 16 mm.

The problem is solved as well by a method for inserting and/or removing of a prosthesis by a tool wherein a head of a tool with a passage is positioned around a shaft of a prosthesis, which is engaged at the neck of the prosthesis by a blocking member, for which an adjustment member is applied at the blocking member via a adjustment element and/or a adjustment thread and an impact power is executed on the prosthesis, especially by an impact element and/or a guiding housing with a tension spring or by a power tool.

Further features and advantages of the invention result from the claims and the following description, in which examples of the subject of the invention are explained in connection with the figures.

DETAILED DESCRIPTION OF THE PREFERRED EMBODIMENT(S)

Figure 1:
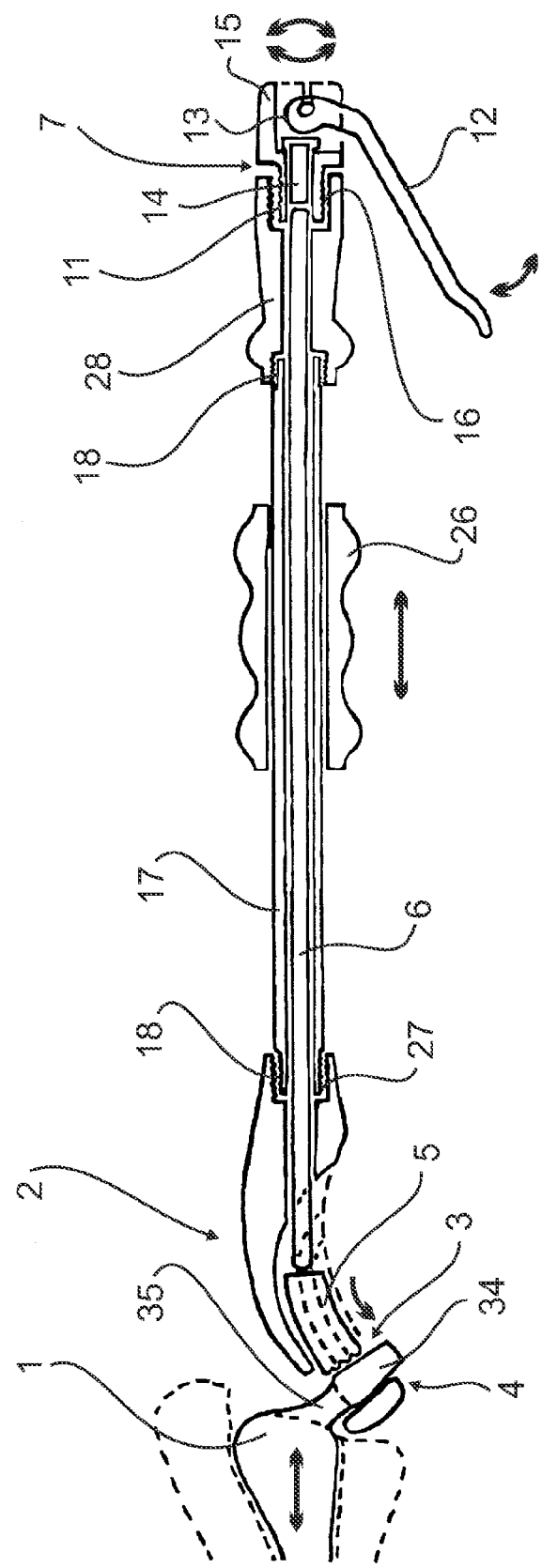
FIG. 1 a surgical tool in longitudinal section,
FIG. 2 a surgical tool in exploded view,
FIG. 3 a surgical tool in perspective view,
FIG. 4 a surgical tool in longitudinal view,
FIG. 5*a* a head of a tool,
FIG. 5*b* a head of a tool in section,
FIG. 6*a* a head of a tool in top view,
FIG. 6*b* an inserting element in top view,
FIG. 6*c* an inserting element in longitudinal section,
FIG. 7*a* a surgical tool with s spring,
FIG. 7*b* a surgical tool with opened side view and
FIG. 7*c* a surgical tool in cross-section.

FIG. 1 shows a surgical tool in a longitudinal view. The surgical tool exhibits a head 2 of a tool, in which passage 3 a neck 4 of a prosthesis 1 is inserted. By a blocking member 5, which is inserted relocatably in the head 2 of the tool, the neck 4 of the prosthesis is fixed. Especially it is possible, if using a inserting element 8 with a conical seating, to insert of a conus 34 of a neck of a prosthesis. The passage 3 can be as well arranged at the concave formed body 35 of the neck of the prosthesis, if there is enough space and the region offers sufficient stability. The adjustment member 5 is put forward by an adjustment member 6, here by means of a pull rod, so far, that the prosthesis is trapped in the passage 3. The adjustment member 6 is routed relocatably hereunto in a guiding housing 17, which is deposited at a head 2 of the tool by a thread 27. At an end 19 which is turned away from the head of the tool the guiding housing 17 has an hold 28, which routes the pull rod to a adjustment housing 15, which is attached to the hold 28. The connection between hold 28 and adjustment housing 15 is established by an adjustment thread 16, which makes an adjustment of the distance between the adjustment housing 15 and the head of the tool possible.

In the adjustment housing 15 an adjustment element 7 in terms of a lever 12 is arranged with an eccentric head 13 of the lever, which is arranged in the adjustment housing 15. By pivoting of the lever 12, the head of the lever exerts an engaging force upon the pull rod via a contact element 14 and hence on the act on blocking member 5. By means of the adjustment thread 16 the distance between pull rod and blocking element 5 is regulated in such a way, that by pivoting of the lever 12 the adjustment contact to the blocking member 5 is made, so that the blocking member 5 is fixing the neck of the prosthesis in the passage 3 of the head 2 of the tool. The prosthesis is hence held by the tool and on the other hand no one of the adjustment devices is in the operation field, where it can come to a damage of the success of the operation.

On the guiding housing 17 an impact element 26 is mounted relocatably, which is suitable for executing an impact power against the end of the guiding housing 17. The impact power is transported by the rigid connection between the guiding housing 17 and the head 2 of the tool to the prosthesis 1, which hence can be inserted or unfastened depending on the direction of the force. If the impact element 26 is hit against the end 19 which is turned away from the head of the tool, of the guiding housing 17 or against a stopper, which is connected thereto, the prosthesis is inserted.

Figure 2:
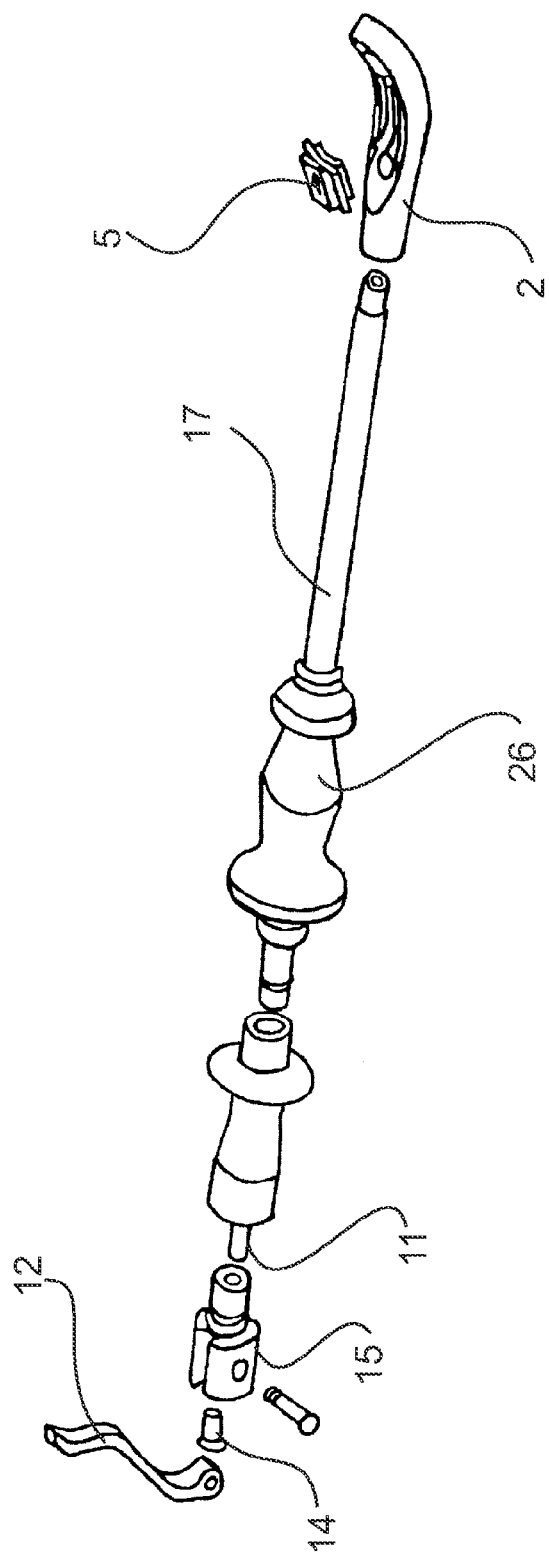

FIG. 2 shows a surgical tool in exploded view. The components of the tool are easily screwed together by some threads, so that an safe force transport can be managed or the tool can be easily cleaned. The blocking member 5 can be taken out of the head of the tool by simply shifting in the lateral grooves and be cleaned.

Figure 3:
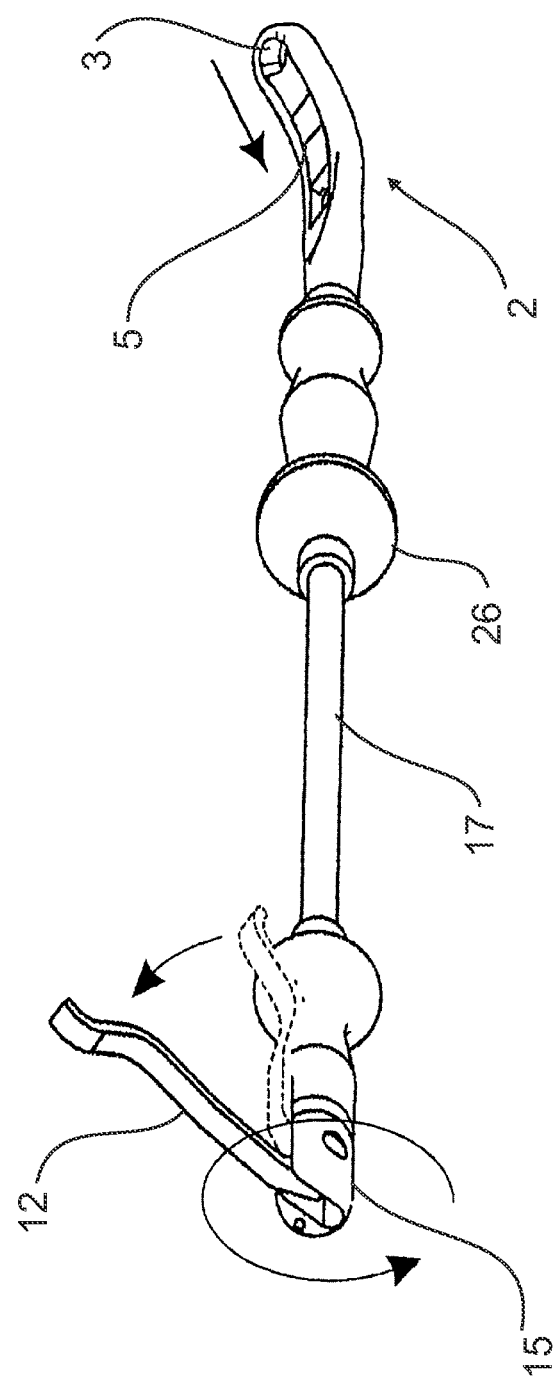

FIG. 3 shows a surgical tool in perspective view. The applying of the tool as well as the application of the force is carried out in a few steps. At first the lever 12 is unloaded so far, that the pull rod releases the blocking member 5 and the blocking member 5 opens the passage 3 in the head 2 of the tool substantially. Then the neck 4 of the prosthesis is inserted into the passage 3. By the adjustment thread at the adjustment housing 15 the pull rod is introduced far at the blocking member 5. The fixing of the pull rod is takes place by the expanding of the lever 12, whereby the eccentric mounted head of the lever engages the pull rod to the blocking member 5 via the contact element 14, where the blocking member is put at the neck 4 of the prosthesis. Now the impact force can be applied in the preferred direction with the impact element 26, which is routed on the guiding housing 17.

Figure 4:
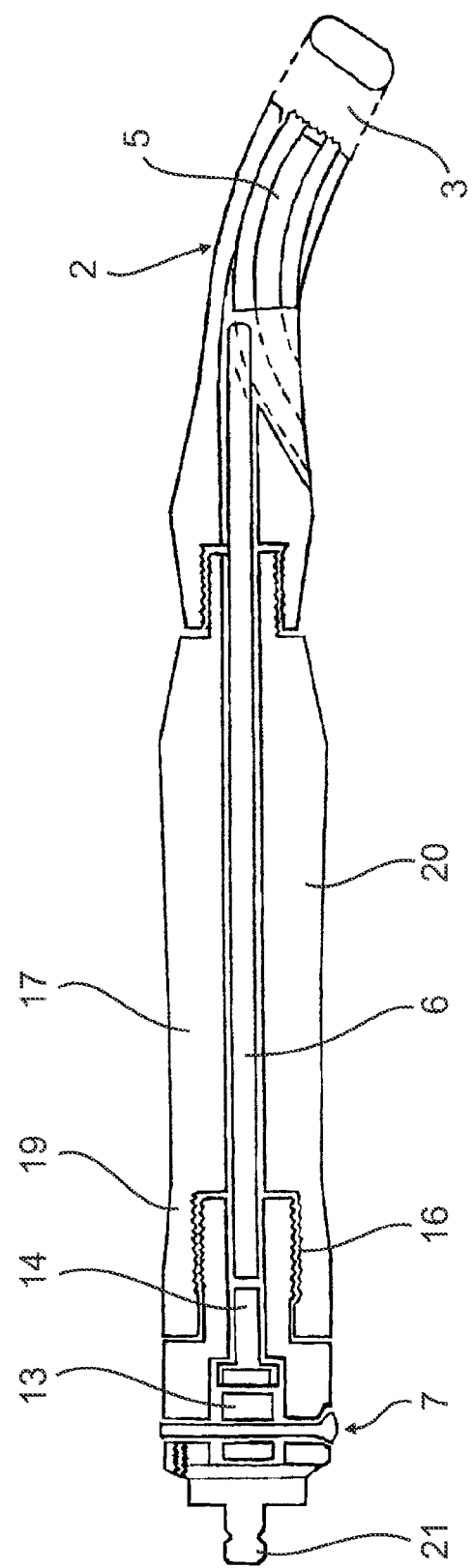

FIG. 4 shows a surgical tool in a longitudinal section. The tool shows a head 2 of the tool with a blocking member 5 and a passage 3. At the head of the tool a guiding housing 17 is installed by means of a thread, whereby the guiding housing serves as a hand hold 20 at the same time. At the end 19 of the guiding housing 17, which is turned away from the head of the tool, an adjustment housing 15 with an adjustment element 7 in form of a not shown lever with a head 13 of the lever is mounted by means of an adjustment thread 16. This head 13 of the lever is—via a contact element 14—in contact with an adjustment member 6 in form of an pull rod, which fixes the blocking member 5 in the head 2 of the tool at the neck of the prosthesis. For the impacting of the impact force the adjustment housing 15 has an adapter 21, at which a not shown power tool is engageable, by which a impacting force is applyable preferably in two different directions onto the tool, by what on the one hand a solving of the prosthesis is possible and on the other hand a fixation of the prosthesis.

FIG. 5a shows a head 2 of the tool with a lateral opening 29, through which a neck of a prosthesis is to be inserted into the passage 3. This is especially important for prosthesis, which are produced in one part, named monobloc prostheses, which is especially the case for older and cheaper prostheses.

FIG. 5b shows a head 2 of a tool in section, where the opening 29 is clearly visible. The head 2 of the tool has grooves 30, into which the respectively formed blocking member is insertable.

FIG. 6a shows a head 2 of the tool in top view, which has an lateral opening 29, through which a neck 4 of a prosthesis into the passage 3. The head 2 of the tool hence shows grooves 30 for the inserting of the blocking member 5.

FIG. 6b shows an inserting element 8 in top view, which is insertable into the passage 3 of a head 2 of the tool for example according to FIG. 6a and facilitates a homogeneous distribution of the forces. The passage 3 doesn't must have necessary a lateral opening 29, but this facilitates the insertion of the neck 4 of the prosthesis. The insertion element 8 shows a lateral opening 32 and an inner diameter 10 of its seating 33, which can be chosen adapted to the necks 4 of the prostheses.

FIG. 6c shows an insertion element 8 according to FIG. 6b in the longitudinal view. The insertion element 8 shows an conically tapered inner surface 9, whereby a good fitting to conically tapered conus 34 of the neck of the tools is possible.

Figure 7A:
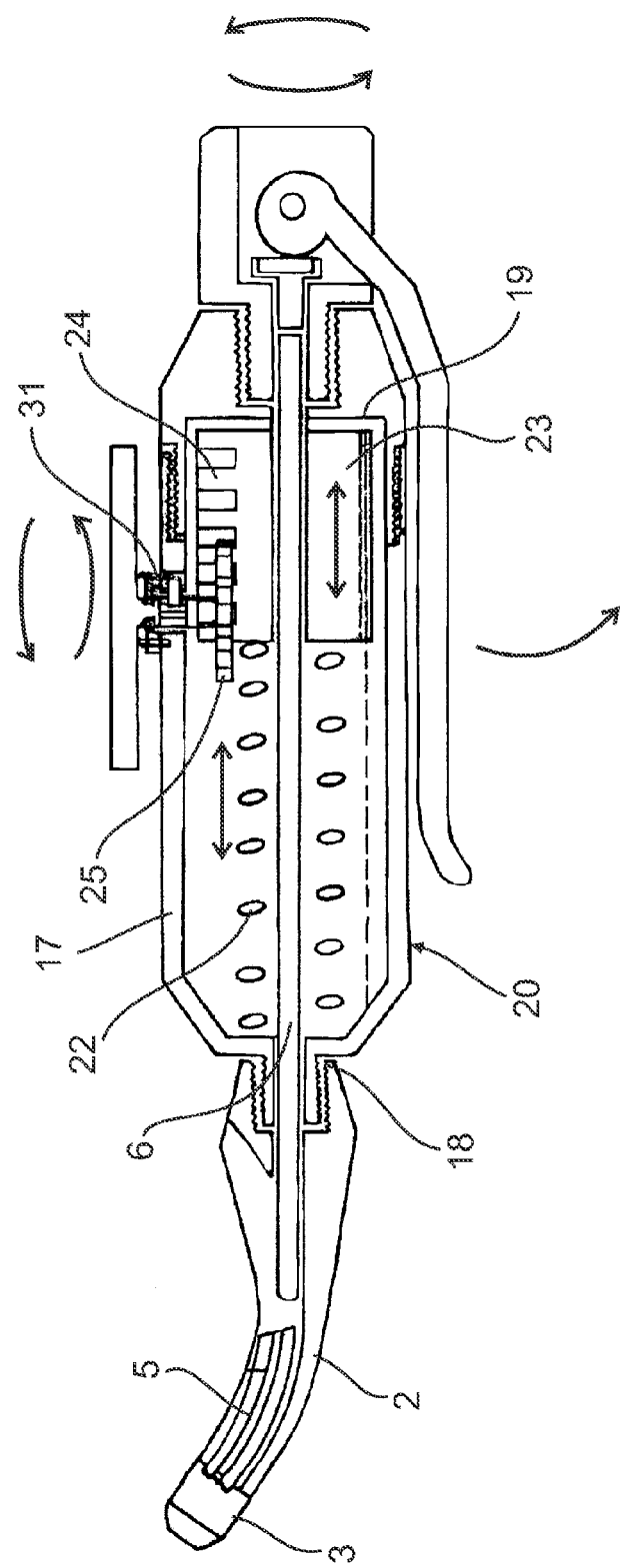

FIG. 7a shows a surgical tool with a tension spring 22. The tension spring 22 is inserted into a guiding housing 17 and is acted upon by an impact-/holding element 23 at one side. This impact-/holding element 23 can be clamped by turning of a gear 25, which is shown as a half in the example, on a pull rod 24, which is fastened at an impact-/holding element 23. Thereby the engaging element 31 engages in each turning position and fixes the gear 25 in its turning position so long until the half wheel is turned to the side, at which it shows no teeth. This results in that the engaging element 31 has no hold any more and that the impact-/holding element 23 is beaten against an end 19 which is turned away from the head of the tool by the force of the spring. The force executed hereby is transported via the guiding housing 17 to the head of the tool and from that to the prosthesis, which is solved by the impact. If the spring were engaged in the guiding housing in that way, that the impact-/holding element 23 would strike at the other end of the guiding housing, the inserting force for the inserting of the prosthesis would be generated. The tool with the tension spring 22 in the guiding housing 17 is provided very compactly and safely and is able to be inserted in narrow operations fields.

Figure 7B:
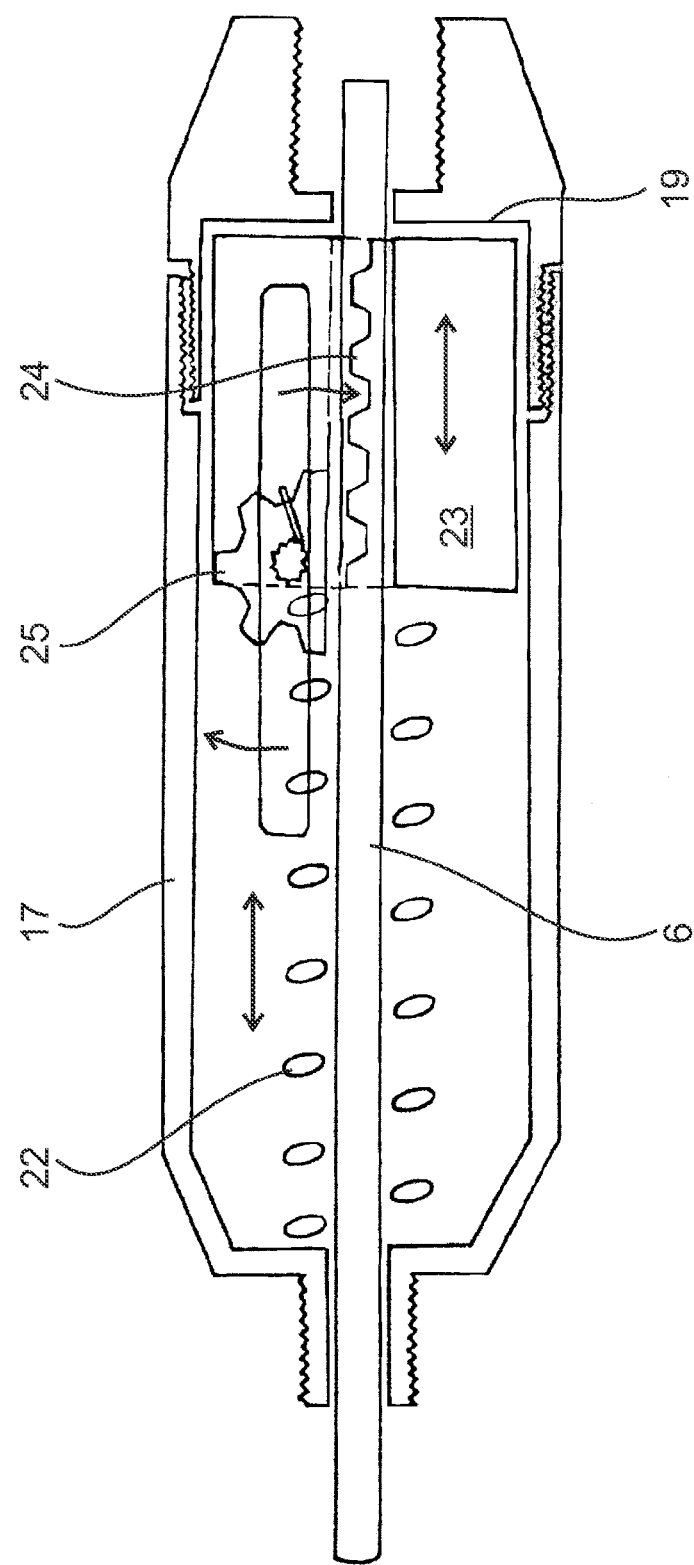

FIG. 7b shows a surgical tool with an opened side view. The gear 25 is presented in lateral view, whereby the lower side of the gear has no teeth.

FIG. 7c shows a surgical tool in sectional view, whereby the gear 25 engages in a recess of the impact-/holding element 23.

LIST OF REFERENCE NUMERALS 1 prosthesis
2 head of the tool
3 passage
4 shaft of the prosthesis
5 blocking member
6 adjustment member
7 adjustment element
8 inserting element
9 inner surface
10 inner diameter
11 end which is turned away from the heard of the tool 12 lever
13 head of lever
14 contact element
15 adjustment housing
16 adjustment thread
17 guiding housing
18 end which is turned towards the heard of the tool
19 end which is turned away from the heard of the tool
20 hand hold
21 adapter
22 tension spring
23 impact-/holding element
24 gear rod
25 gear
26 impact element
27 thread
28 hold
29 opening
30 groove
31 engaging element
32 opening
33 seating
34 conus of neck of prosthesis
35 body of neck of prosthesis

The invention claimed is:

1. A surgical tool for knocking out or inserting a prosthesis, comprising an elongated shaft having a continuously curved tool head which comprises a passage adapted for insertion of a prosthesis neck,
   a bolt mechanism configured to detachably block said prosthesis neck when it is inserted within said passage, and
   an at least partially compressible insertion element which is inserted into said passage of said tool head, said insertion element being configured to receive said prosthesis neck,
   said bolt mechanism comprising an adjustable blocking element extending from said tool shaft into said passage, wherein a position of said blocking element is adaptable to different diameters of a neck of the prosthesis, and a controlling member configured to apply an adjusting force onto the blocking element and comprising a rod inserted moveably within said tool shaft and adjacent to said blocking element and an adjustment element configured to actuate said rod at an end of said rod which is turned away from the tool head,
   wherein an actuation of said blocking element is arranged to move said blocking element and to releasably lock said blocking element in a blocking position in said tool head, and
   wherein said tool head comprises a lateral opening at said passage for lateral insertion of the prosthesis neck.

2. The surgical tool of claim 1, wherein said insertion element has a lateral aperture, and said insertion element is inserted into the passage of the laterally opened tool head of the tool such that lateral apertures of said tool head and said insertion element coincide.

3. The surgical tool of claim 1, wherein the insertion element has a tapered seat and has an inner diameter which corresponds to the respective diameter of a conical neck of the prosthesis.

4. The surgical tool of claim 1, wherein the adjustment element is provided by a cam lever having an eccentric cam which acts upon the end of the rod which is turned away from the tool, wherein said surgical tool is configured so that an axial position of the blocking element along said tool shaft is dependent on a pivoting angle of said cam lever.

5. The surgical tool of claim 4, further comprising a contact element made of plastic arranged between a head of said cam lever and an end of the pull rod which is turned away from the head of the tool, wherein said contact element, is elastic and able to transfer a force from said cam lever to said rod.

6. The surgical tool of claim 1, wherein the adjustment element is an adjustment housing having a thread for adjustment, wherein the thread is configured to allow adjustment of the distance between the tool head and the adjustment housing.

7. The surgical tool of claim 6, wherein said tool shaft comprises as thread for connecting to said adjustment housing and configured to allow fine adjustment at the end facing away from said tool head.

8. The surgical tool of claim 6, wherein said tool shaft comprises a thread connecting to a handle, wherein said handle is connected to said adjustment housing by means of a thread for the adjustment of the distance.

9. The surgical tool of claim 6, wherein the tool shaft has on its outer diameter a slidable impact grip which is slidable between said tool head and said adjustment housing.

10. The surgical tool of claim 6, further comprising an adapter at said adjustment housing for attaching a power tool to said surgical tool for applying an impact power to said blocking member which is engaged to the prosthesis in said tool head.

11. The surgical tool of claim 1, wherein said tool shaft through which said rod is guided has a thread for connecting said tool shaft and said tool head.

12. The surgical tool of claim 1, wherein the tool shaft is configured as a handle.

13. The surgical tool of claim 1, wherein the blocking element is guided by opposing grooves which are formed in the head of the tool.

14. The surgical tool of claim 1, wherein the blocking element is dimensioned to engage necks of prostheses having a diameter between 8 to 12 mm.

15. The surgical tool of claim 1, wherein the blocking element is dimensioned to engage necks of prostheses having a diameter between 11 and 16 mm.

16. A surgical tool for knocking out or inserting a prosthesis, comprising an elongated shaft having a continuously curved tool head which comprises a passage adapted for insertion of a prosthesis neck,
   a bolt mechanism configured to detachably be said prosthesis neck when it is inserted within said passage,
   an at least partially compressible insertion element which is inserted into said passage of said tool head, said insertion element being configured to receive said prosthesis neck, and
   a tension spring situated in the tool shaft, wherein said tension spring is arranged to be loaded by means of an impact/holding element arranged at said tool shaft, which can be locked and unlocked, and wherein after unlocking said impact/holding element said tension spring is arranged to apply an impulse due to its spring load towards one of the ends of said tool shaft for releasing or insertion of said prosthesis,
   said bolt mechanism comprising an adjustable blocking element extending from said tool shaft into said passage, wherein a position of said blocking element is adaptable to different diameters of a neck of the prosthesis and a controlling member configured to apply an adjusting force onto the blocking element
   wherein said tool head comprises a lateral opening at said passage for lateral insertion of the prosthesis neck.

17. The surgical tool of claim 16, further comprising a rack and pinion actuator which is arranged between said tool shaft and said impact/holding element and configured to load said tension spring by moving the impact/holding element.

* * * * *